United States Patent
Farnan et al.

(10) Patent No.: US 9,566,375 B2
(45) Date of Patent: Feb. 14, 2017

(54) METHODS FOR ESTABLISHING SUPPLEMENTAL BLOOD FLOW IN THE CIRCULATORY SYSTEM

(75) Inventors: Robert C. Farnan, Rivervale, NJ (US); Oliver Marseille, Aachen (DE); Wolfgang Kerkhoffs, Aachen (DE)

(73) Assignee: CircuLite, Inc., Teaneck, NJ (US)

( * ) Notice: Subject to any disclaimer, the term of this patent is extended or adjusted under 35 U.S.C. 154(b) by 1452 days.

(21) Appl. No.: 13/022,105

(22) Filed: Feb. 7, 2011

(65) Prior Publication Data

US 2011/0137234 A1 Jun. 9, 2011

Related U.S. Application Data

(60) Division of application No. 11/846,839, filed on Aug. 29, 2007, now Pat. No. 7,905,823, and a
(Continued)

(51) Int. Cl.
*A61M 1/10* (2006.01)
*A61M 1/12* (2006.01)
(Continued)

(52) U.S. Cl.
CPC ............... *A61M 1/12* (2013.01); *A61M 1/122* (2014.02); *A61M 25/04* (2013.01); *A61M 25/0662* (2013.01)

(58) Field of Classification Search
CPC ........ A61M 1/12; A61M 1/122; A61M 25/04; A61M 25/0662
(Continued)

(56) References Cited

U.S. PATENT DOCUMENTS 5,300,107 A 4/1994 Stokes et al.
5,338,301 A 8/1994 Diaz
(Continued)

FOREIGN PATENT DOCUMENTS

EP 213748 A1 3/1987
EP 0381062 A2 8/1990
(Continued)

OTHER PUBLICATIONS

Japanese Patent Office, Notice of Reasons for Rejection in JP Application No. 2010-523013, Dec. 11, 2012.
(Continued)

*Primary Examiner* — Christopher D Koharski
*Assistant Examiner* — Michael Carey
(74) *Attorney, Agent, or Firm* — Wood Herron & Evans LLP

(57) ABSTRACT

A blood circulation assist system comprising an inflow cannula having a lumen and an insertion device configured to be received therein and to facilitate insertion of a portion of the inflow cannula into a heart chamber. The insertion device includes a shaft having distal and proximal end portions and a plurality of lumens. A first lumen is configured to receive a guidewire and a second lumen is configured to receive a pressurized fluid. A tip connected to the distal end portion of the shaft is configured for insertion into the heart chamber. The tip has a hollow interior communicating with the first shaft lumen. An inflatable member is coupled to the distal end portion of the shaft and includes a hollow interior in fluid communication with the second shaft lumen. The inflatable member is movable between deflated and inflated configurations for releasably securing the insertion device to the inflow cannula.

13 Claims, 9 Drawing Sheets

Related U.S. Application Data continuation-in-part of application No. PCT/US2007/076956, filed on Aug. 28, 2007.

(60) Provisional application No. 60/823,971, filed on Aug. 30, 2006.

(51) Int. Cl.
*A61M 25/04* (2006.01)
*A61M 25/06* (2006.01)

(58) Field of Classification Search
USPC .......................................... 600/16; 606/153
See application file for complete search history.

(56) References Cited

U.S. PATENT DOCUMENTS

| | | | |
|---|---|---|---|
| 5,449,342 | A | 9/1995 | Hirose et al. |
| 5,478,309 | A | 12/1995 | Sweezer et al. |
| 5,676,670 | A | 10/1997 | Kim |
| 5,797,960 | A | 8/1998 | Stevens et al. |
| 5,944,745 | A | 8/1999 | Rueter |
| 6,669,708 | B1 * | 12/2003 | Nissenbaum .......... A61B 17/11 604/164.04 |
| 6,926,662 | B1 | 8/2005 | Aboul-Hosn et al. |
| 6,955,175 | B2 | 10/2005 | Stevens et al. |
| 7,317,951 | B2 | 1/2008 | Schneider et al. |
| 7,699,864 | B2 | 4/2010 | Kick et al. |
| 7,713,193 | B2 | 5/2010 | Nance et al. |
| 7,722,568 | B2 | 5/2010 | Lenker et al. |
| 7,780,692 | B2 | 8/2010 | Nance et al. |
| 2002/0010425 | A1 | 1/2002 | Guo et al. |
| 2003/0033396 | A1 | 2/2003 | McCall |
| 2004/0153112 | A1 | 8/2004 | Nissenbaum et al. |
| 2004/0236170 | A1 | 11/2004 | Kim |
| 2005/0033396 | A1 | 2/2005 | Ospyka |
| 2005/0065589 | A1 | 3/2005 | Schneider et al. |
| 2005/0124937 | A1 | 6/2005 | Kick et al. |
| 2005/0288604 | A1 | 12/2005 | Eigler et al. |
| 2006/0052750 | A1 | 3/2006 | Lenker et al. |
| 2006/0135962 | A1 | 6/2006 | Kick et al. |
| 2006/0135963 | A1 | 6/2006 | Kick et al. |
| 2006/0135981 | A1 | 6/2006 | Lenker et al. |
| 2006/0184088 | A1 | 8/2006 | Van Bibber et al. |
| 2006/0200189 | A1 | 9/2006 | Nance et al. |
| 2006/0253102 | A1 | 11/2006 | Nance et al. |
| 2006/0270893 | A1 | 11/2006 | Bolling et al. |
| 2007/0043324 | A1 | 2/2007 | Shibata et al. |
| 2008/0200943 | A1 | 8/2008 | Barker et al. |
| 2008/0215008 | A1 | 9/2008 | Nance et al. |
| 2008/0243081 | A1 | 10/2008 | Nance et al. |
| 2009/0112050 | A1 | 4/2009 | Farnan et al. |
| 2009/0254166 | A1 | 10/2009 | Chou et al. |
| 2009/0287182 | A1 | 11/2009 | Bishop et al. |
| 2009/0287183 | A1 | 11/2009 | Bishop et al. |
| 2010/0145267 | A1 | 6/2010 | Bishop et al. |
| 2010/0228077 | A1 | 9/2010 | Lenker et al. |

FOREIGN PATENT DOCUMENTS

| | | |
|---|---|---|
| EP | 745409 A1 | 12/1996 |
| EP | 1205147 A1 | 5/2002 |
| JP | 2297380 A | 12/1990 |
| JP | 10305094 A | 11/1998 |
| JP | 2001504365 A | 4/2001 |
| JP | 2002177284 A | 6/2002 |
| JP | 2007020972 A | 2/2007 |
| WO | 9819629 A2 | 5/1998 |
| WO | 0027312 A1 | 5/2000 |
| WO | 2004082742 A1 | 9/2004 |
| WO | 2004091716 A1 | 10/2004 |
| WO | 2005037345 A2 | 4/2005 |
| WO | 2008027869 A2 | 3/2008 |

OTHER PUBLICATIONS

United States Patent and Trademark Office, Advisory Action in related U.S. Appl. No. 12/392,623, dated Mar. 7, 2012, 15 pp.
United States Patent and Trademark Office, Interview Summary in related U.S. Appl. No. 12/392,623, dated Feb. 13, 2012, 1 pg.
United States Patent and Trademark Office, Final Office Action in related U.S. Appl. No. 12/392,623, dated Oct. 18, 2012, 22 pp.
United States Patent and Trademark Office, Non-final Office Action in related U.S. Appl. No. 12/392,623, dated May 10, 2011, 23 pp.
United States Patent and Trademark Office, Non-final Office Action in related U.S. Appl. No. 12/392,623, dated Nov. 24, 2010, 38 pp.
European Patent Office; Supplemental Search Report in European Patent Application No. 08835271, Jun. 12, 2014.

* cited by examiner

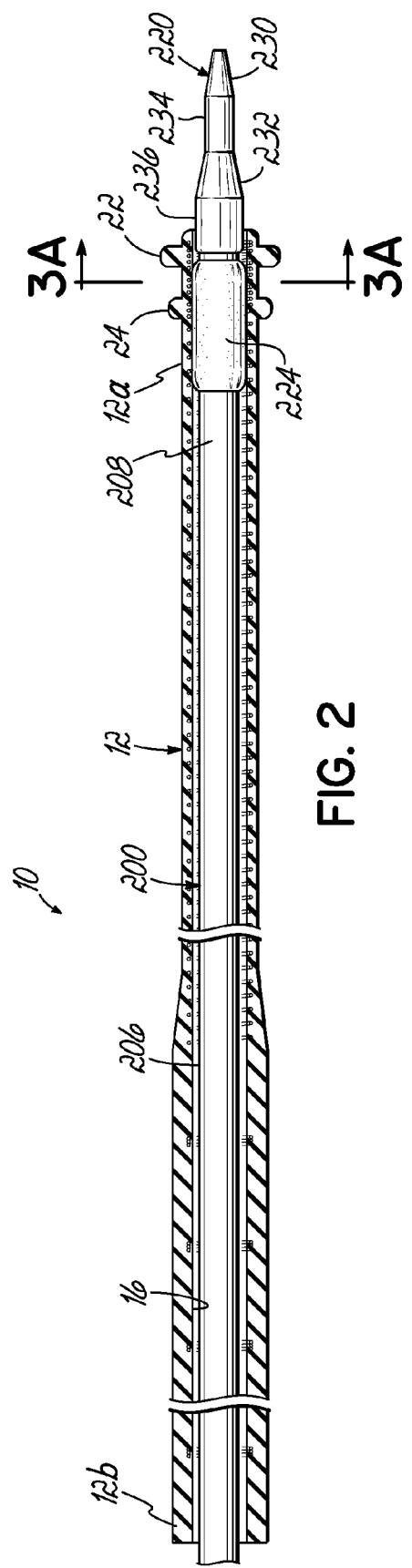

US 9,566,375 B2

METHODS FOR ESTABLISHING SUPPLEMENTAL BLOOD FLOW IN THE CIRCULATORY SYSTEM

CROSS REFERENCE

This application is a divisional of U.S. application Ser. No. 11/846,839, filed Aug. 29, 2007, now U.S. Pat. No. 7,905,823, which is a continuation-in-part of PCT Application Serial No. PCT/US07/76956 filed on Aug. 28, 2007 (expired), which claims the priority benefit of U.S. Provisional Patent Application Ser. No. 60/823,971, "Devices, Methods and Systems for Establishing Supplemental Blood Flow in the Circulatory System," filed Aug. 30, 2006, the disclosures of which are expressly incorporated by reference herein in their entirety. This application is also generally related to co-pending U.S. patent application Ser. No. 11/846,886, filed Aug. 29, 2007, now U.S. Pat. No. 8,333,686, entitled "Cannula Insertion Devices, Systems, And Methods Including A Compressible Member," filed on even date herewith, which is expressly incorporated by reference herein in its entirety.

TECHNICAL FIELD

This invention generally relates to medical devices and methods and, more particularly, to methods and devices for fluid coupling to the heart of a patient in systems for assisting blood circulation in a patient.

BACKGROUND

Various devices and methods have been utilized to conduct blood from the heart to assist with blood circulation in a patient. This is often desirable or necessary in cases where a patient is experiencing congestive heart failure and a transplant organ has either not been located, or the patient is not a suitable candidate for a transplant. The blood pumps are typically attached directly to the left ventricle of the heart, however, at least one blood pump system locates the pump remotely, such as subcutaneously in the manner of a pacemaker. In this regard, see U.S. Pat. No. 6,530,876, the disclosure of which is hereby fully incorporated by reference herein. In this situation or similar situations, a cannula may be used to create an inflow conduit from the heart (an intra-thoracic location) to a pump located in a superficial (non-thoracic cavity) location, which may be the so-called "pacemaker pocket." Of course, other remote locations are possible as alternatives. The pacemaker pocket is a location usually accessed by a surgical incision generally parallel to and below the collarbone extending down toward the breast, and over the pectoral muscle. Sometimes the pacemaker pocket is made below the muscle. The pump, to which the cannula is connected, is intended to sit in the pectoral pocket and is preferably at, but not limited to, a location on the right side of the chest.

One area in need of improvement is the insertion device, or trocar, used to deliver an inflow conduit or cannula to the heart. It would be desirable to provide an insertion device configured to give a surgeon enhanced control of the location of the tip of the insertion device to minimize trauma to the heart tissue during the process of inserting the tip of the insertion device through an incision or other opening in the heart tissue and into a chamber of the heart and to simplify this procedure resulting in a reduction in surgery time. It would also be desirable to provide an insertion device that may be securely engaged with the inflow cannula during insertion of the cannula into a chamber of the heart, and then disengaged from the cannula for removal.

General cannula implantation methods known and usable in connection with the present invention may involve many different approaches and several of the representative approaches are described further below. For example, the cannula may be implanted by directly invading the thoracic cavity. Surgical methods include so-called open heart surgery in which a median sternotomy is made to fully expose the heart within the thoracic cavity. Still other surgical methods include less invasive surgical methods such as a thoracotomy, mini-thoracotomy, thoracoscopic, or any other less invasive approaches. Any of these or other surgical methods can be used to implant the cannula in fluid communication with any desired location of the heart as described herein.

SUMMARY

Generally, and in one of many aspects, the present invention provides a device for establishing a blood flow conduit between a chamber in a heart of a patient and a remote location, such as a location at which a blood pump resides away from the heart. In this regard, the term "remote," as used herein means away from the heart but is not limited to any particular distance from the heart. The devices and systems of the present invention include an inflow cannula having a lumen, and an insertion device configured to be received within the lumen of the inflow cannula and to facilitate insertion of a portion of the inflow cannula into the chamber of the heart. The insertion device has a shaft having a distal end portion, and a proximal end portion (relative to a surgeon implanting the cannula) and a plurality of lumens formed therein. A first one of the lumens is configured to receive a guidewire therein and a second one of the lumens is configured to receive a pressurized fluid therein. The insertion device further includes a tip connected to the distal end portion of the shaft, with the tip being configured for insertion into the chamber of the heart. The tip has a hollow interior communicating with the first one of the lumens of the shaft. The insertion device also includes an inflatable member coupled to the distal end portion of the shaft and having a hollow interior in fluid communication with the second one of the lumens of the shaft. The inflatable member is movable between a first, deflated configuration and a second, inflated configuration for releasably securing the insertion device to the inflow cannula.

In other embodiments, the system may include one or more of the following features. The system may further include a blood pump having an inlet and an outlet and an outflow cannula coupled at one end thereof to the outlet of the pump and configured to be coupled, at an opposite end thereof, to the arterial system of the patient. A proximal end portion of the inflow cannula may be coupled to the inlet of the blood pump and the distal end portion of the inflow cannula is configured for insertion into the chamber of the heart.

The insertion device may further include a hub connected to the proximal end portion of the shaft. The hub may include a first leg having a first lumen formed therein that communicates with the first one of the lumens in the shaft, and a second leg having a second lumen formed therein and in fluid communication with the second one of the lumens of the shaft. The second leg may be configured for coupling to a source of fluid. The shaft may further include an aperture formed in the distal end portion that is in fluid communication with the second one of the shaft lumens and the hollow interior of the inflatable member, which may be a generally cylindrical sleeve when inflated. In one embodiment, the shaft may include three lumens, with one being configured to receive a guidewire therein and with the other two being in fluid communication with the hollow interior of the inflatable member. The shaft may comprise inner and outer cylindrical extrusions connected by a plurality of circumferentially spaced ribs.

In another aspect, the invention provides a system for inserting a cannula through biologic tissue. The system includes a cannula having a lumen and an insertion device configured to be received within the lumen of the cannula and to facilitate insertion of a portion of the cannula through the biologic tissue. The insertion device includes a shaft having proximal and distal end portions and a tip connected to the distal end portion of the shaft. The tip is configured for insertion through the biologic tissue. The system also includes an expandable member coupled to the distal end portion of the shaft, with the expandable member being movable between a first configuration wherein the expandable member is disengaged with the inflow cannula, and a second configuration wherein the expandable member is releasably secured to the inflow cannula.

In another aspect, the invention provides a method of inserting an inflow cannula having a lumen into a chamber in a heart of a patient. The method includes the step of inserting an insertion device into the lumen of the inflow cannula wherein at least a portion of a tip of the insertion device protrudes beyond a distal end portion of the inflow cannula. The insertion device further includes a shaft, with the tip being secured to a distal end portion of the shaft, and an expandable member coupled to the distal end portion of the shaft. The method further comprises expanding the expandable member to releasably secure the inflow cannula to the insertion device and inserting the tip of the insertion device and a distal end portion of the inflow cannula into the chamber of the heart.

In other embodiments, the method of inserting an inflow cannula into a chamber of the patient's heart may include one or more of the following steps. The expandable member may be an inflatable member and the step of expanding may comprise inflating the inflatable member. This step may include directing a pressurized fluid through a lumen formed in the shaft of the insertion device into a hollow interior of the inflatable member. A puncture may be created in the tissue defining the chamber and the puncture may be gradually dilated with the tip of the insertion device to a larger size to facilitate inserting the distal end portion of the inflow cannula into the chamber of the heart. The inflow cannula may be secured to tissue of the heart defining the chamber and the expandable member may be disengaged from the cannula after securing the cannula to the heart tissue.

In another aspect, the invention provides a method of inserting a cannula having a lumen through biologic tissue. The method includes the step of inserting an insertion device into the lumen of the cannula wherein at least a portion of a tip of the insertion device protrudes beyond a distal end portion of the cannula. The insertion device further includes a shaft, with the tip being secured to a distal end portion of the shaft, and an expandable member coupled to the distal end portion of the shaft. The method further includes expanding the expandable member to releasably secure the cannula to the insertion device and inserting the tip of the insertion device and the distal end portion of the cannula through the tissue.

Various additional features and aspects will be more readily appreciated upon review of the following detailed description of the illustrative embodiments taken in conjunction with the accompanying drawings.

BRIEF DESCRIPTION OF THE DRAWINGS

FIG. 2 is a cross-sectional view of an inflow cannula with an insertion device according to an embodiment of the present invention extending through a lumen of the inflow cannula, and with an inflatable member of the insertion device inflated to releasably secure the insertion device to the inflow cannula.

DETAILED DESCRIPTION OF THE ILLUSTRATIVE EMBODIMENTS

Figure 1:
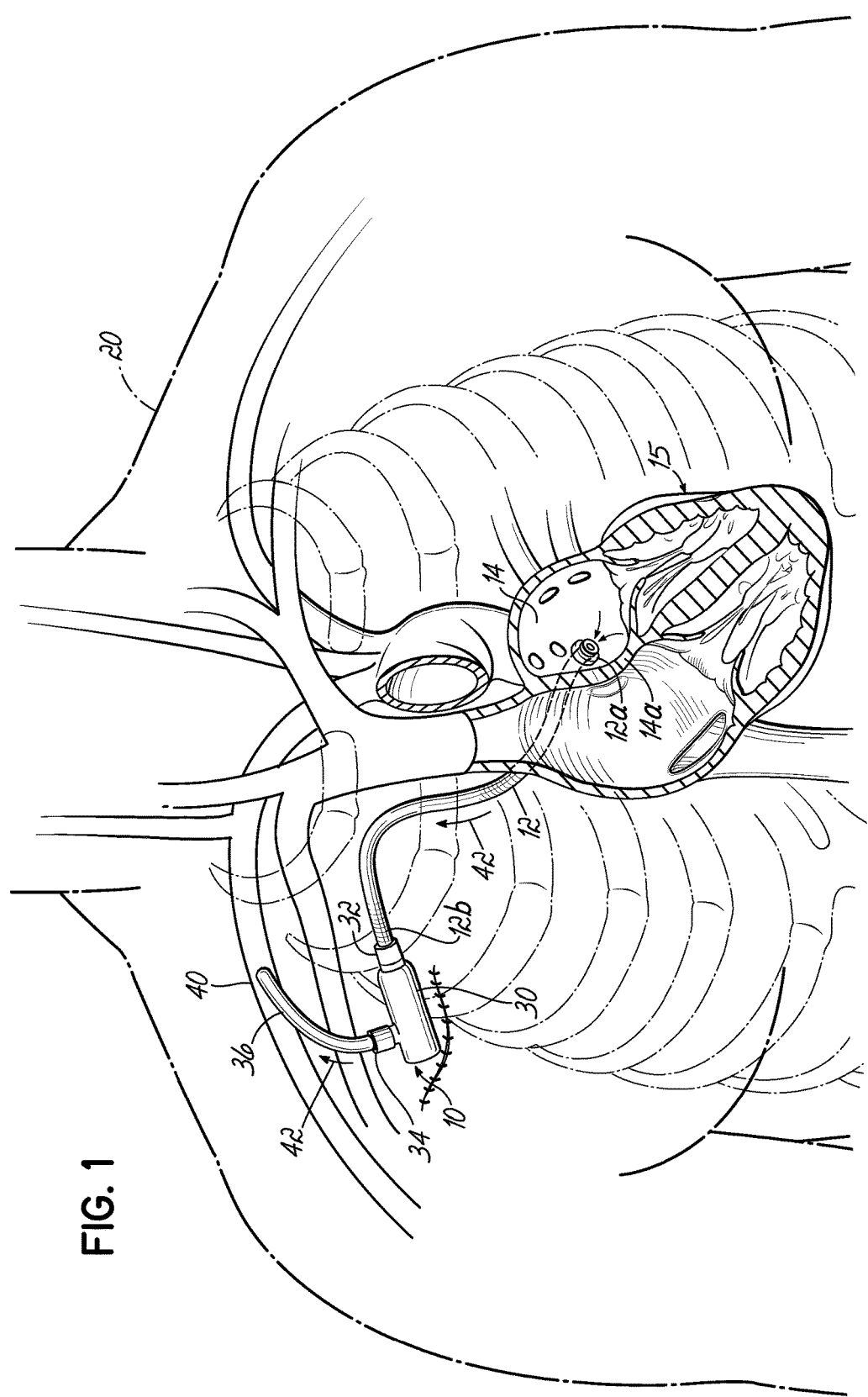
FIG. 1 is a schematic representation of chest anatomy, and illustrates one example of a pathway, exterior to the venous system, used to access a patient's heart and implant a circulatory assist system in accordance with an embodiment of the invention.

FIG. 1 illustrates one of many possible general configurations of a blood circulation assist system 10 implanted in accordance with the inventive aspects. Devices and systems configured in accordance with the teachings herein may be implanted in any suitable surgical manner, including but not limited to those discussed generally herein, and may be used to insert a cannula through heart tissue into a chamber of the heart. Devices and systems configured in accordance with the inventive aspects may also be used to insert a cannula through other biologic tissue, for example through kidney tissue into an interior chamber of the kidney.

System 10 includes an inflow cannula 12 that includes a distal end portion 12a that passes into the left atrium 14 of the heart 15 of patient 20. Access may be made, for example, into any portion within the left side of the heart (e.g., the left atrium and/or left ventricle) to access oxygenated blood. The inflow cannula 12 is attached directly to an exterior wall of the heart 15 on the left side, such as to the left atrial wall 14a as shown in FIGS. 7F-7G. The inflow cannula 12 may be directed to the exterior area of the heart through any desired surgical approach, such as one of the approaches generally discussed subsequently. Cannula 12 includes a distal anchor element 22 and a proximal anchor element 24 that have a disc-like configuration in the illustrative embodiment. However, anchor elements 22, 24 can have other configurations, such as illustrated in previously referenced U.S. Patent Application Ser. No. 60/823,971. Cannula 12 may be made of various implant or medical grade materials, such as silicone.

The blood circulation assist system 10 also includes a blood pump 30, having an inlet 32 and an outlet 34, and an outflow cannula 36. A proximal end portion 12b of inflow cannula 12 is coupled to the inlet 32 of blood pump 30. Any suitable blood pump 30 may be used, including those described in U.S. Pat. Nos. 6,176,848; 6,116,862; 6,942,611; and 6,623,475 or DE 10 2004 019 721.0. The outflow cannula 36 is connected between the outlet 34 of the pump 30 and an artery, such as the superficial axillary artery 40. Blood flow therefore travels in the direction of the arrows 42 from the left atrium 14, through the pump 30, and into the patient's arterial system through the outflow cannula 36. The outflow cannula 36 may be connected to a superficial artery, such as the axillary artery 40, through a suitable surgical incision and attachment procedure which may involve the use of suitable grafts (not shown) and suturing (not shown).

The inflow and/or outflow cannulas 12, 36 may be connected to blood pump 30 prior to or after implantation of pump 30. The inflow and/or outflow cannulas 12, 36 may first be cut to a suitable length by an appropriate sterilized cutting tool (not shown), such that the system may be more easily implanted into, for example, a pectoral pacemaker pocket without kinking of cannulas 12, 36 as illustrated in previously referenced U.S. Provisional Patent Application Ser. No. 60/823,971.

The inflow cannula 12 may be delivered to heart 15 using an insertion device 200 according to one embodiment of the present invention, in conjunction with any suitable surgical procedure. The insertion device 200 has multiple functions associated with a cannula, such as inflow cannula 12. These functions include: provision of an expandable member that is used to releasably secure the insertion device 200 to a cannula, such as inflow cannula 12, which enhances the ability of a surgeon to deliver the cannula to a desired access location and to insert the cannula through biologic tissue, that may be heart tissue, while minimizing trauma to the tissue due to the stiffness of the combination of the cannula and the insertion device 200; and gradually dilating an opening in the tissue, such as a puncture or incision, to a larger size to facilitate inserting a distal end portion of the cannula through the biologic tissue. One illustrative procedure is discussed subsequently with reference to FIGS. 2 and 7A-7G. FIGS. 2 and 7B-7E illustrate insertion device 200 inserted into a lumen 16 of the inflow cannula 12, over a guidewire 50 with insertion device 200 releasably secured to inflow cannula 12.

Figure 3A:
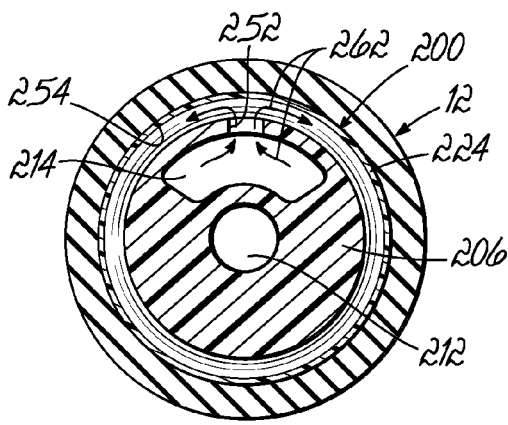
FIG. 3A is a cross-sectional view taken along line 3A-3A in FIG. 2A with the inflatable member of the insertion device inflated.
Figure 3B:
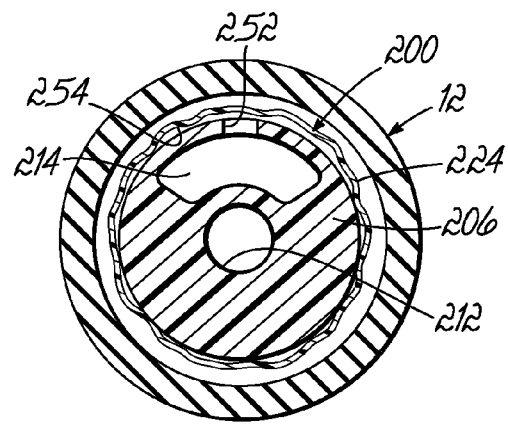
FIG. 3B is a cross-sectional view taken along line 3B-3B in FIG. 7F with the inflatable member of the insertion device deflated.
Figure 4:
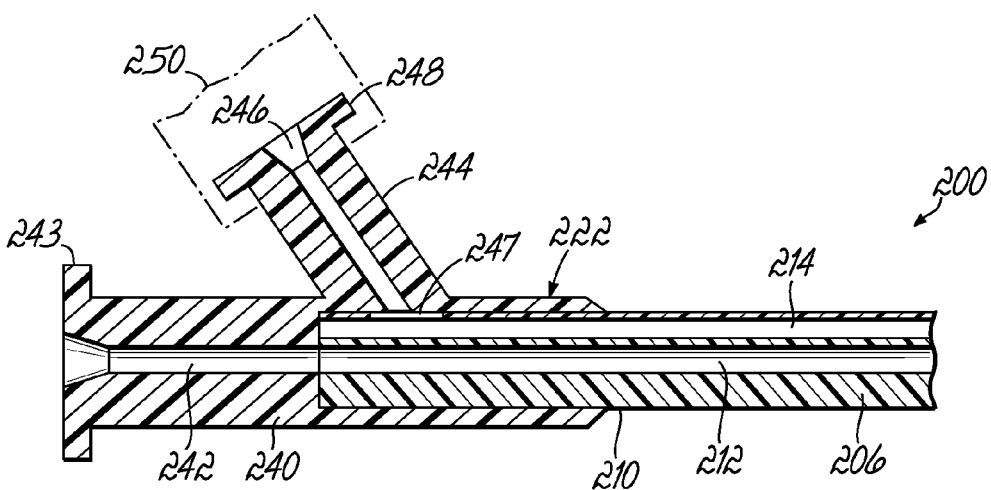
FIG. 4 is a cross-sectional view of the hub, and a portion of the shaft, of the insertion device shown in FIGS. 2, 3A and 3B.

Insertion device 200 includes a shaft 206 having a distal end portion 208 (FIG. 2), a proximal end portion 210 (FIG. 4) and lumens 212, 214 formed therein (shown in FIGS. 3A, 3B and 4). Lumen 212 is configured to accept any commercially available guidewire therein, such as guidewire 50. Lumen 214 is configured to receive a pressurized fluid therein, typically a sterile liquid, that may be received from a syringe, for example, as discussed further in greater detail. Lumens 212, 214 do not communicate with one another. Shaft 206 may be made from materials having a high durometer. In one embodiment, these materials may have a durometer of 63D or higher. Examples of suitable materials include, but are not limited to, thermoplastic materials such as nylon, urethane and plastic material sold under the trademark Pebax®. Any other suitable biocompatible material may be used to make shaft 206.

Insertion device 200 further includes a tip 220 connected to the distal end portion 208 of shaft 206, a hub 222 connected to the proximal end portion 210 of shaft 206 and an expandable member 224 coupled to the distal end portion 208 of shaft 206. In the illustrated embodiment, expandable member 224 is more particularly an inflatable member. However, as subsequently discussed in greater detail, other insertion devices having different expandable members may be used in accordance with the inventive aspects. Inflatable member 224 may extend at least partially around the distal end portion 208. Inflatable member 224 may be a balloon-like expandable member as used, for example, in conventional balloon catheters. FIGS. 2, 3A, 7C, 7D and 7E illustrate the inflatable member 224 inflated, or expanded, which releasably secures the insertion device 200 to inflow cannula 12. FIGS. 3B and 7F illustrate the inflatable member deflated or collapsed so that insertion device 200 does not engage inflow cannula 12 and therefore is not temporarily secured to inflow cannula 12.

Tip 220 includes a hollow interior 226 (FIG. 7C) that communicates with lumen 212 of shaft 206 to receive guidewire 50. An inside diameter of tip 220 is sized to accommodate a commercially available guidewire, such as guidewire 50, and is typically larger than the outside diameter of the guidewire by about 0.003 inch or more. As subsequently discussed with reference to FIGS. 7B-7E, the guidewire 50 protrudes beyond tip 220 into chamber 14 of heart 15 during the initial steps of this procedure. Tip 220 is configured for insertion into chamber 14 of heart 15 and to facilitate insertion of inflow cannula 12 into chamber 14. The configuration of tip 220 causes a gradual dilation of an incision in the heart tissue, in this case the left atrial wall 14a, to a larger size that is sufficient to receive the inflow cannula 12. This gradual dilation may be achieved by a tip such as tip 220 having a stepped configuration as shown in FIGS. 2 and 7B-7F, or alternatively, with a tip (not shown) having a continuous taper. In either event, the tip converges from a proximal end portion to a distal end portion.

Tip 220 may include tapered portions 230, 232 and cylindrical portions 234, 236. Tapered portion 230 is a distal end portion of tip 220 in the illustrated embodiment and is integral with cylindrical portion 234. Tapered portion 232 is integral with cylindrical portion 234 and cylindrical portion 236, which is the proximal end portion of tip 220 in the illustrated embodiment. Alternatively, the tip of insertion device 200 may include additional tapered and cylindrical portions. Each of the cylindrical portions of tip 220, in this case cylindrical portions 234, 236, has a unique outside diameter, with the outside diameters progressively increasing in size from a distal most one of the cylindrical portions, in this case cylindrical portion 234, to a proximal most one of the cylindrical portions, in this case cylindrical portion 236. For example, cylindrical portion 234 has an outside diameter $d_1$ and cylindrical portion 236 has an outside diameter $d_2$ that is greater than $d_1$ (FIG. 7D). The number of tapers incorporated in the tip of insertion device 200 is dependent upon the inside diameter of the inflow cannula. In one embodiment, if the inside diameter of the inflow cannula, such as inflow cannula 12, is about 6 mm, the tip of insertion device 200 may include two tapers, such as tip 220. In this example, the diameter $d_1$ of the cylindrical portion 234 may be about 2 mm and the diameter $d_2$ of the cylindrical portion 236 may be about 4 mm. However, diameters $d_1$ and $d_2$ may have different magnitudes, depending upon the inside diameter of the inflow cannula, such as inflow cannula 12. If, for example, the anatomy is not large enough to support a tip having a stepped configuration, such as tip 220, a tip (not shown) may be provided with a continuous taper. For example, if the dimension across a chamber of the heart (from location of entry to an opposite wall) into which a tip is to be inserted is less than the overall length of a tip having multiple tapers, then a shorter tip with one continuous taper would be used.

Tip 220 may be made from a thermoplastic material, for example, nylon, urethane, or plastic material sold under the trademark Pebax® and may include a filler material that is radiopaque, for example, barium or tungsten. The filler material may be a metallic paste. Tip 220 may also be made from any other suitable biocompatible base and filler materials. Additional features, for example, dimpling (not shown) may be added to tip 220 to enhance the visibility of tip 220 if a transesophageal echocardiogram procedure or the equivalent, is to be used during placement of the insertion device 200.

As best shown in FIG. 4, hub 222 is configured to provide access to the lumens 212, 214 of shaft 206. In the illustrated embodiment, hub 222 has a leg 240 that extends along the distal end portion 210 of shaft 206 and includes a lumen 242 that communicates with lumen 212 of shaft 206. Accordingly, lumen 242 may receive the guidewire 50. Leg 240 of hub 222 may include a luer thread 243 conforming to ISO 594 or an equivalent, to permit flushing of lumen 242 before and/or after use of insertion device 200.

Hub 222 further includes a leg 244 that may be angled relative to leg 240 and includes a lumen 246 that is in fluid communication with lumen 214 of shaft 206, for purposes of inflating or deflating the inflatable member 224. Shaft 206 includes at least one aperture 247, which may be a notch, formed therein proximate hub 222 to establish this fluid communication. Leg 244 is adapted for coupling to a source of fluid, typically a liquid such as a saline solution, which can be pressurized. This may be accomplished by providing a proximal end portion of leg 244 with a luer thread 248 conforming to ISO 594 or an equivalent, to receive a syringe 250. Lumen 246 of leg 244 of hub 222 is in fluid communication with a hollow interior of syringe 250, which is adapted to contain fluid therein. An aperture 252, which may be a notch or skive, (FIGS. 3A and 3B) is formed in a portion of shaft 206 that is covered by the inflatable member 224 and provides fluid communication between lumen 214 of shaft 206 and a hollow interior 254 of inflatable member 224.

Hub 222 may be made from a material that is typically used for catheter applications. Examples of suitable materials include, but are not limited to, a polycarbonate and nylon. Hub 222 may also be made from any other suitable biocompatible material. Hub 222 may be secured to shaft 206 by an adhesive or other conventional means and is sized to accommodate the outside diameter of the particular shaft to which it is secured.

The inflatable member 224 is typically positioned proximate tip 220, as illustrated in FIGS. 2, and 7C-7F, and may be secured to shaft 206. An adhesive, a melting or welding process, or other suitable means or processes may be used to secure the inflatable member 224 to shaft 206. Inflatable member 224 is used to releasably secure the inflow cannula 12 to the insertion device 200 when member 224 is inflated, in view of the flexibility of the inflow cannula 12, to assist a surgeon in directing the inflow cannula to the desired access location on the heart 15. This provides stiffness to at least a distal end portion 12a of the inflow cannula 12.

The inflatable member 224 may be a generally cylindrical sleeve when inflated. Inflation may be achieved by extending the plunger (not shown) of syringe 250, which pressurizes the fluid therein, causing the fluid to flow through lumen 246 of leg 244 of hub 222 and into lumen 214 of shaft 206. The fluid then flows from lumen 214 through aperture 252 in shaft 206 and into the hollow interior 254 of inflatable member 224 as illustrated by arrows 262 in FIG. 3A.

The length of inflatable member 224, i.e., the longitudinal distance along shaft 206, varies depending upon the desired stiffness of the distal end portion 12a of inflow cannula 12 and the associated contact surface between the outer surface of inflatable member 224 and the inner surface of inflow cannula 12 when the inflatable member 224 is inflated. For example, the length of the inflatable member 224 may vary from about 5 mm to about 50 mm, depending upon the particular application. The outside diameter of inflatable member 224, when member 224 is inflated, may be sized to provide about 0 to about 1 mm of interference with the inner surface of inflow cannula 12.

Inflatable member 224 may be made from a thermoplastic material, for example nylon, PET, polyethylene, polyurethane or plastic material sold under the trademark Pebax®. Inflatable member 224 may also be made from any other suitable biocompatible material. The material used to make inflatable member 224 typically has a rated burst pressure of at least 2 atm. The wall thickness of inflatable member 224 for the particular length of inflatable member 224 is directly related to the desired burst pressure, the material properties and the inflation diameter of inflatable member 224. Hooke's Law for thin-walled cylinders may be used to determine the wall thickness of inflatable member 224.

After the distal end portion 12a of the inflow cannula 12 is inserted into chamber 14 at the desired position and is secured to the heart 15 with purse string sutures, for example, the inflatable member 224 is deflated. Deflation may be achieved by retracting the plunger of syringe 250 which causes the fluid to flow from the hollow interior 254 of the inflatable member 224 back into syringe 250. The volume of the lumen 214 in shaft 206 is sized to permit the inflatable member 224 to be inflated and deflated within an acceptable time period, for example, about 30 second or less. After inflatable member 224 has been deflated, the insertion device 200 may be withdrawn from the inflow cannula 12.

Figure 5:
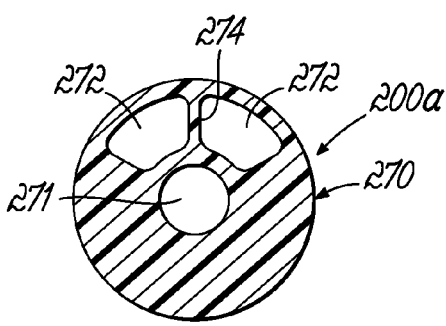
FIG. 5 is a cross-sectional view of a shaft of an insertion device according to another embodiment of the present invention.

FIG. 5 illustrates an insertion device 200a that is the same as insertion device 200 except that insertion device 200a includes a shaft 270 instead of shaft 206 of insertion device 200. Shaft 270 includes a lumen 271, similar to lumen 212 of shaft 206, to accept guidewire 50. Instead of a relatively larger, outer lumen such as lumen 214 in shaft 206, shaft 270 includes two relatively smaller outer lumens 272, separated by a rib 274 that extends along the length of shaft 270. Each of the lumens 272 is in fluid communication with the hollow interior 254 of the inflatable member 224 and the source of pressurized fluid, in this case syringe 250. Shaft 270 includes the appropriate apertures, which may be notches or skives (not shown), in the proximal and distal end portions to provide fluid communication between the lumens 272 and the lumen 246 of leg 244 of hub 222 and the hollow interior 254 of the inflatable member 224, respectively. Incorporation of rib 274 enhances the structural characteristics of shaft 270.

Figure 6:
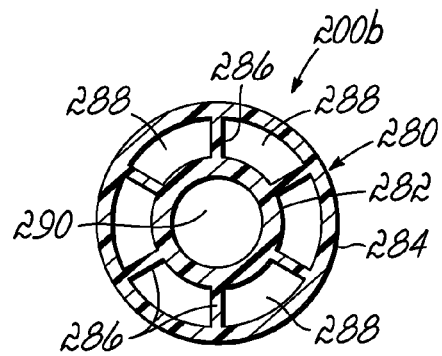
FIG. 6 is a cross-sectional view of a shaft of an insertion device according to another embodiment of the present invention.

FIG. 6 illustrates an insertion device 200b that is the same as insertion device 200 except that insertion device 200b includes a shaft 280 instead of shaft 206 of insertion device 200. Shaft 280 includes an inner 282 and outer 284 cylindrical extrusions that are concentrically positioned and interconnected by a plurality of circumferentially spaced ribs 286. Extrusions 282, 284 and ribs 286 define outer lumens 288. Each of the outer lumens 288 is in fluid communication with the hollow interior 254 of the inflatable member 224, and the source of pressurized fluid, in this case syringe 250. Shaft 280 includes the appropriate apertures, which may be notches or skives (not shown), in the proximal and distal end portions to provide fluid communication between lumens 288 and the lumen 246 of leg 244 of hub 222 and the hollow interior 254 of the inflatable member 224, respectively. Shaft 280 further includes an inner lumen 290 to receive guidewire 50.

Another alternate insertion device (not shown) may be similar to insertion device 200 but may further include a stiff hypotube that surrounds a multi-lumen inner shaft made of a more flexible material such as thermoplastic material. The hypotube may be made of metal, for example, stainless steel. The hypotube increases the column strength of the insertion device relative to a device such as insertion device 200. The alternate insertion device may further include an inner strain relief and an outer strain relief. The inner strain relief may be added to the construction to provide a barrier between the multi-lumen inner shaft and the hypotube while providing a stiffness transition proximal to the included inflatable member. The inner strain relief is typically a thin-walled tube and may be made from a thermoplastic material, for example, plastic material sold under the trademark Pebax®, nylon or polyurethane, but may also be made from a heat-shrink tube, such as a polyester tube. The inner strain relief may be secured to the hypotube at its most proximal end (e.g., near the included hub of the insertion device) and this may be accomplished by the use of an adhesive or heat melting process, for example. Typically, the distal end of the inner strain relief is not secured in place. This allows for relative movement between the multi-lumen inner shaft and the inner strain relief if the insertion device is placed into a curve during insertion. The outer strain relief may extend distal to the hypotube and terminate proximal to the distal end of the inner strain relief. This positioning provides a stiffness gradient from the stiffest component of the insertion device, i.e., the hypotube, to the most flexible component, i.e., the multi-lumen inner shaft. The outer strain relief may be made from a thermoplastic material, such as plastic material sold under the trademark Pebax®, nylon or polyurethane, but may also be made from a heat shrink tube, such as polyester or polyolefin tube. Incorporation of the inner and outer strain reliefs help prevent kinking of the insertion device at locations transitioning from a relatively larger diameter component to a relatively smaller component.

One illustrative procedure for connecting the inflow cannula 12 to heart 15 is shown in FIGS. 7A-7G. In this regard, an access location 300 (FIG. 7A) such as the so-called Waterson's groove is exposed or otherwise accessed during a surgical procedure. A puncture 302 (FIG. 7B) may be made in wall 14a of heart 15 at the access location 300 with a hollow needle 304 to access the interior of the left atrium 14 to allow for the insertion of the distal end portion 12a of cannula 12. In alternate surgical procedures a small incision may be made with a scalpel, in lieu of puncture 302 made with needle 304, to access the interior of the left atrium 14. The diameter of the lumen of needle 304 must be large enough to allow passage of guidewire 50 through needle 304.

Figure 7A:
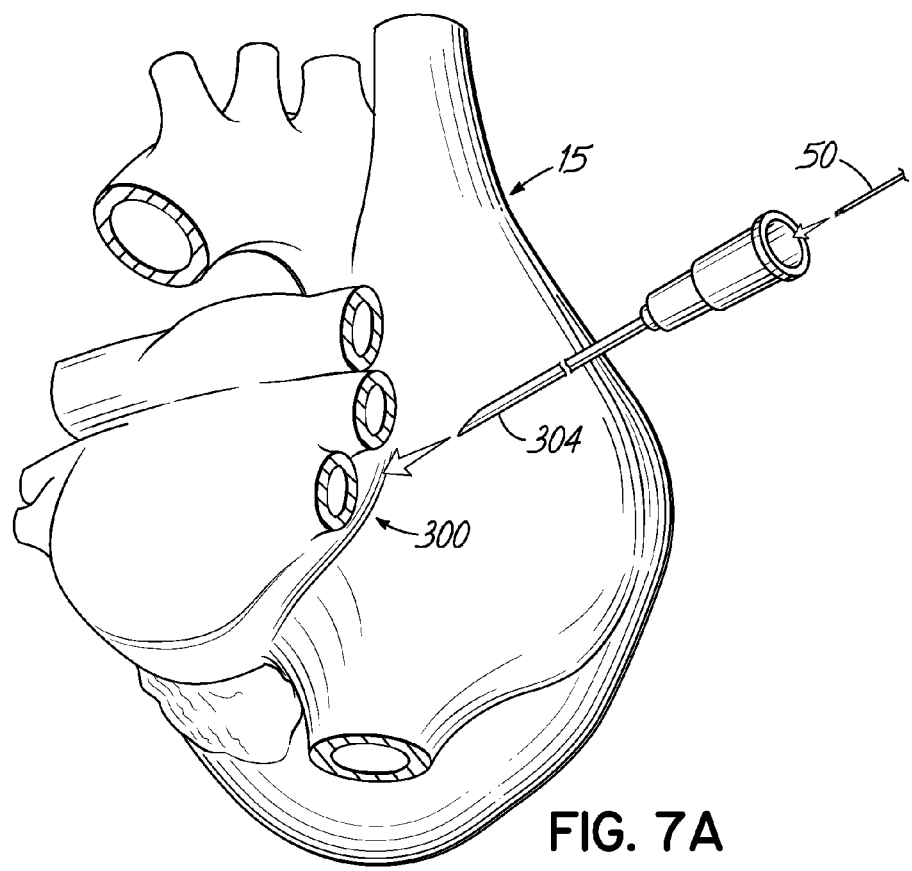
FIG. 7A is an enlarged view of the heart illustrating an access location to the interior of the heart.
Figure 7B:
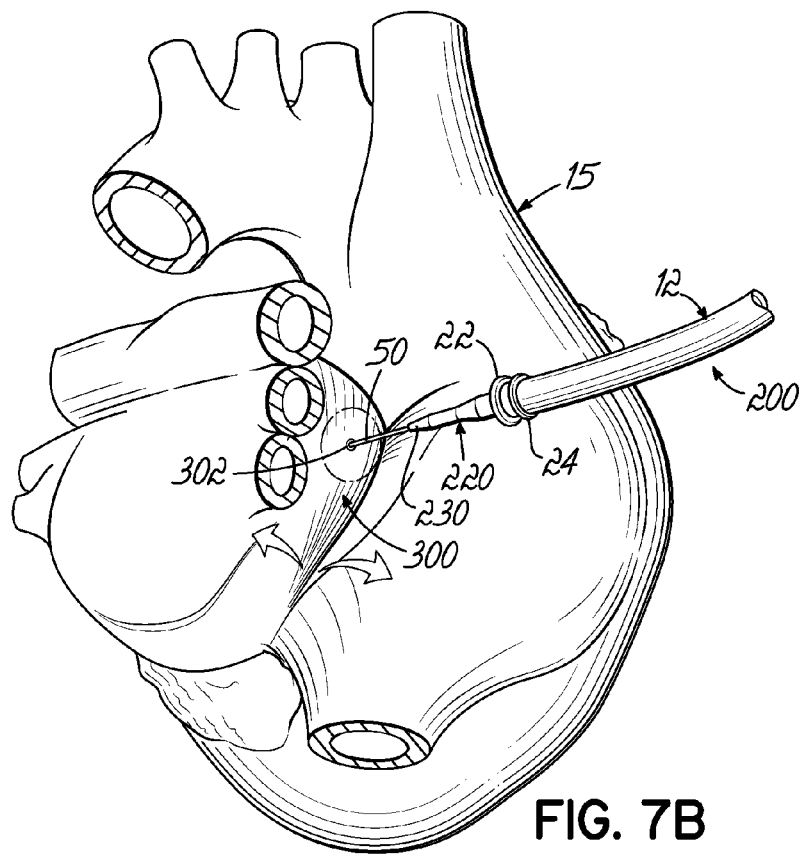
FIG. 7B is a view similar to FIG. 7A, but illustrating the access location exposed and generally showing an inflow cannula being directed toward the access location with the insertion device and a guidewire extending beyond the distal end portion of the inflow cannula.

FIG. 7B illustrates inflow cannula and insertion device 200 delivered to a location proximate heart 15, with guidewire 50 inserted through puncture 302 into the left atrium 14. The guidewire 50 is typically looped within atrium 14 to help avoid any trauma to the heart tissue by the distal tip 50a of the guidewire 50. As shown in FIGS. 7C-7F, one or more purse string sutures 306, 308 may be secured around the puncture 302 in preparation for the insertion of cannula 12.

Figure 7C:
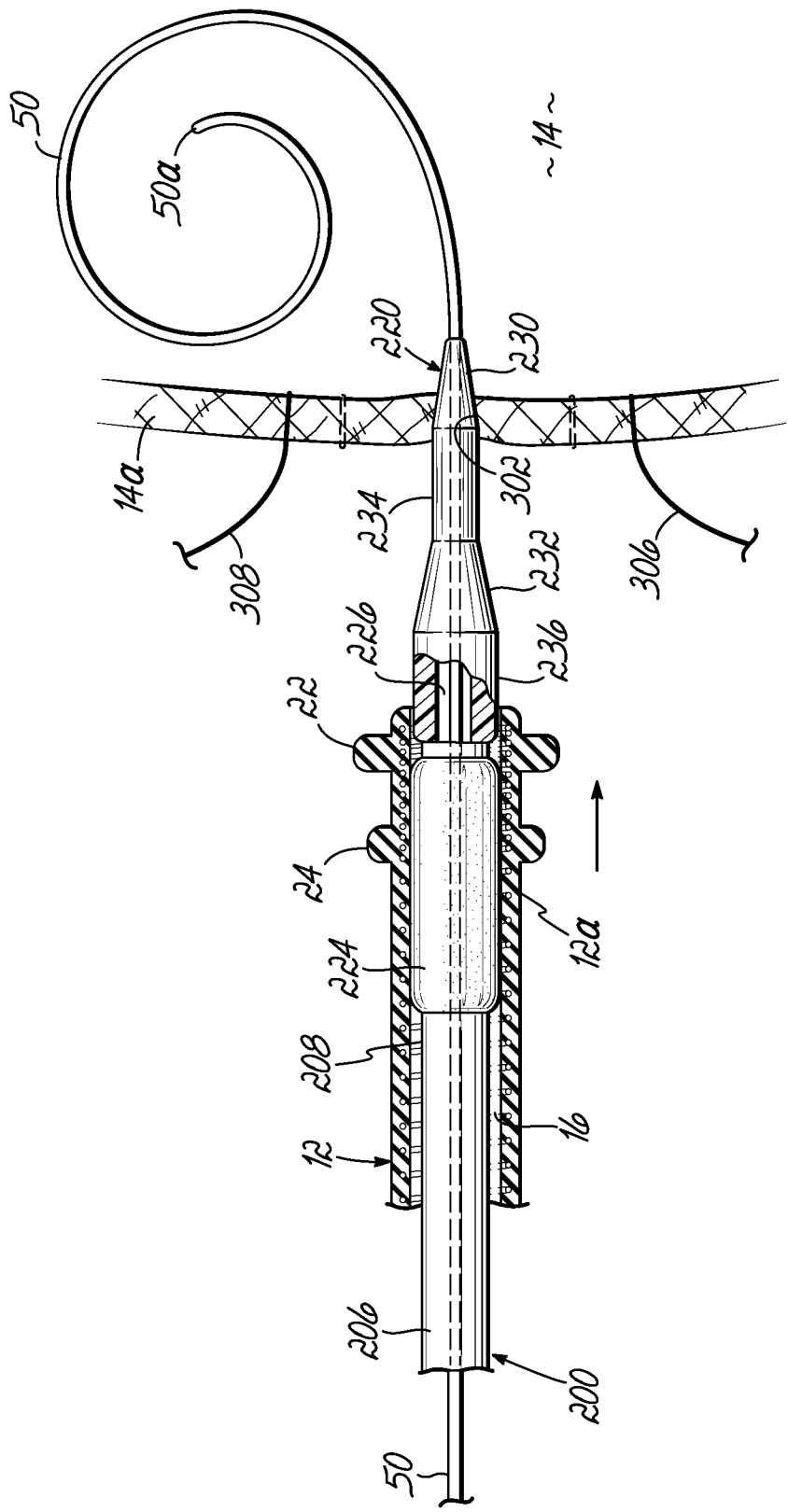
FIG. 7C is a fragmentary cross-sectional view of the heart illustrating a subsequent portion of the procedure, with the guidewire and a portion of a tip of the insertion device inserted into the left atrial chamber or left atrium of the heart, and with the inflatable member of the insertion device inflated to releasably secure the insertion device to the inflow cannula.
Figure 7D:
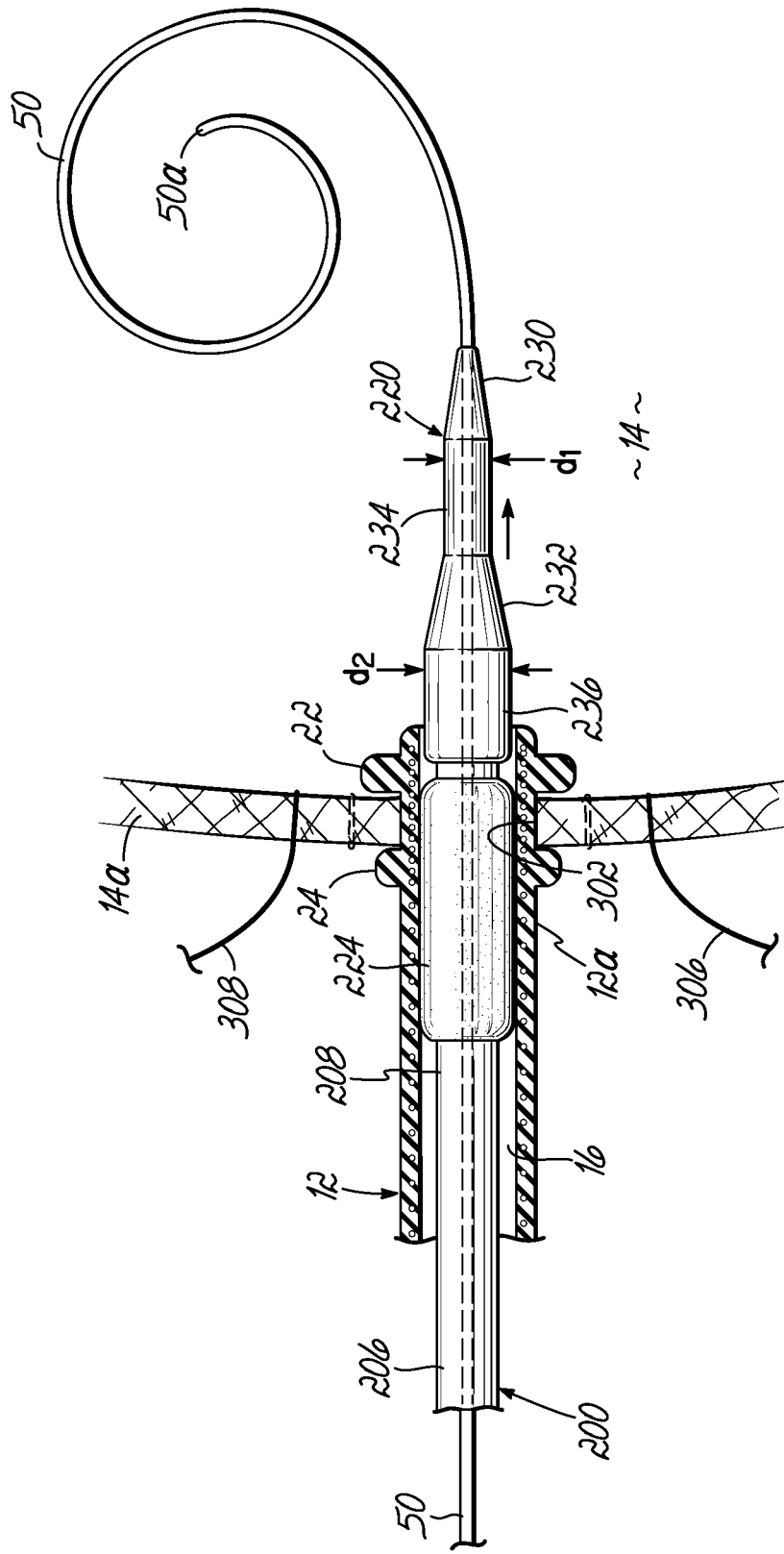
FIG. 7D is a fragmentary cross-sectional view similar to FIG. 7C, illustrating a subsequent portion of the procedure, with the entire tip of the insertion device and the distal end portion of the inflow cannula, including the distal element of the cannula, inserted into the left atrium and with the associated purse string sutures loosened.

FIG. 7C illustrates the step of advancing the tip 220 of insertion device 200 across the left atrial wall 14a over the guidewire 50. The inflatable member 224 is inflated during the steps illustrated in FIGS. 7C-7E to temporarily and releasably secure the insertion device 200 to inflow cannula 12. The stiffness of insertion device 200 permits the surgeon to deliver the insertion device 200 and inflow cannula 12 accurately to the access location 300 and to insert the tip 220 of insertion device 200 through puncture 302 while minimizing trauma to the heart tissue. Inflatable member 224 can remain inflated until sutures 306, 308 are tightened as subsequently discussed.

FIG. 7D illustrates a subsequent step with the entire tip 220 of insertion device 200, the distal end portion 12a of cannula 12, and the distal anchor element 22 of cannula 12 inserted into the left atrium 14. In some procedures, the inflow cannula 12 may be inserted into left atrium 14 such that the distal and proximal anchor elements 22, 24 are initially inserted into the left atrium 14. In this instance, the inflow cannula 12 is then withdrawn slightly proximally (toward the surgeon) to position the proximal anchor element 24 outside the left atrium 14 while leaving the distal anchor element 22 inside the left atrium 14, as shown in FIG. 7D. The material of the anchor elements 22, 24 may be a pliable and/or resilient material such as surgical grade silicone or any other suitable biocompatible material. The anchor elements 22, 24 may collapse when passing through wall 14a of heart 15, and may expand to their original shape once inserted into the left atrium 14 due to the characteristics of the material of anchor elements 22, 24. Alternatively, the anchor elements 22, 24 may be expanded or collapsed by any suitable mechanism operated by the surgeon. Additionally, the proximal anchor element 24 may have a smaller diameter than the distal anchor element 22, so that the smaller proximal anchor element 24 may noticeably pop through puncture 302 leaving the distal anchor element 22 as a firm stop against the opposite side of wall 14a of heart 15, which provides perceptible feedback to the surgeon.

Figure 7E:
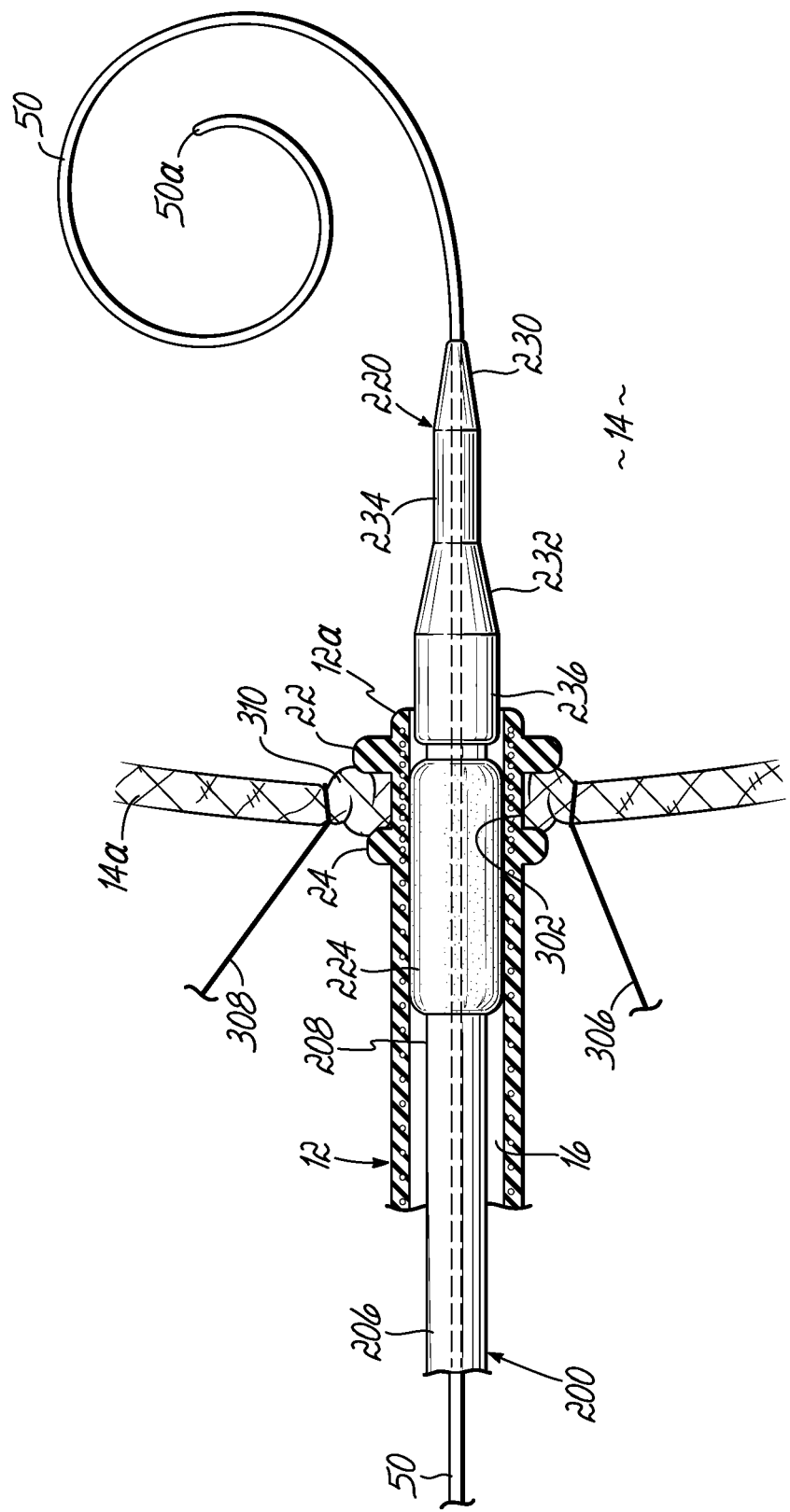
FIG. 7E is a fragmentary cross-sectional view similar to FIG. 7D, illustrating a subsequent portion of the procedure, but with the purse string sutures tightened illustrating the gathering of tissue between the proximal and distal anchor elements of the inflow cannula.
Figure 7F:
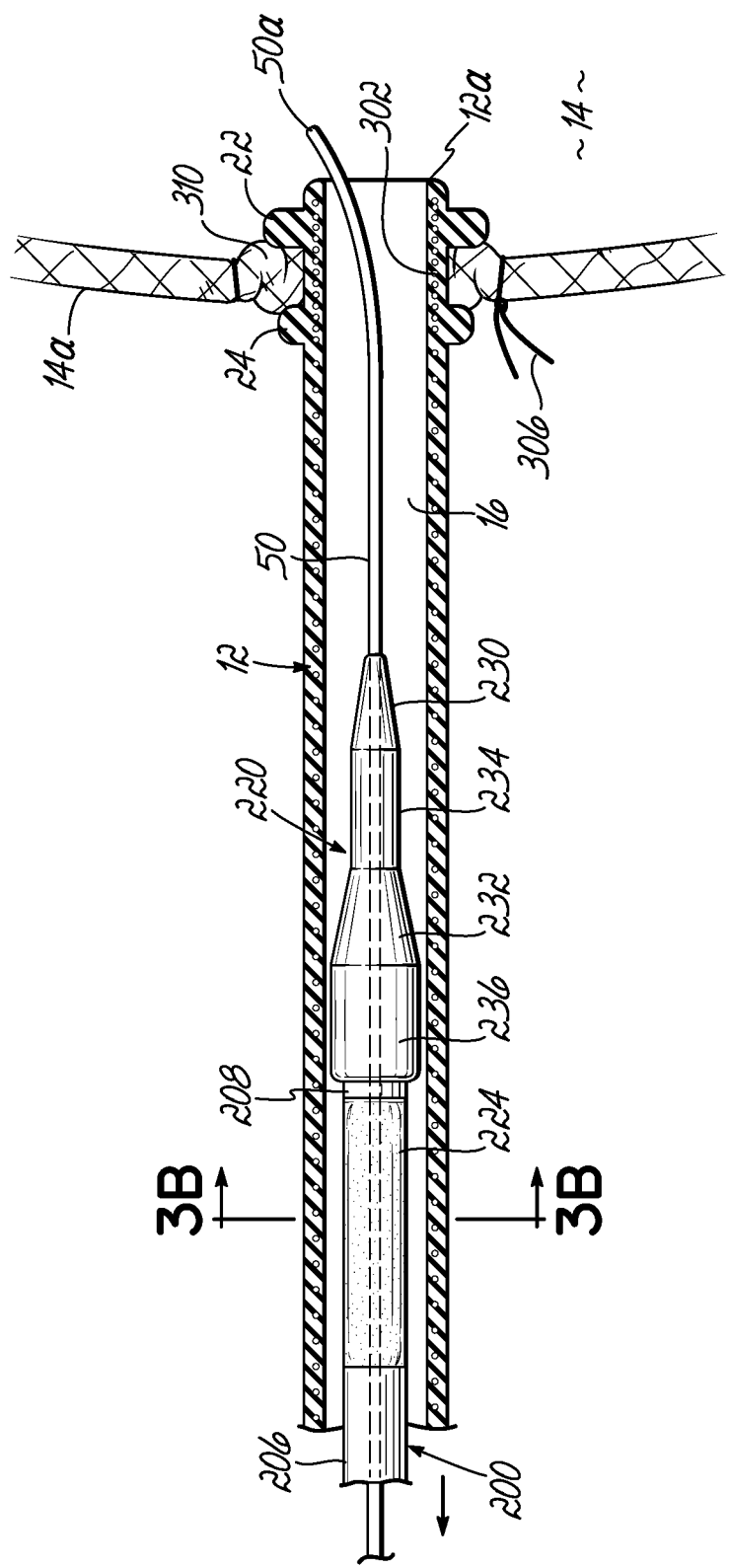
FIG. 7F is a cross-sectional view similar to FIG. 7E, illustrating a subsequent portion of the procedure, with the insertion device and guidewire in the process of being removed from the inflow cannula.
Figure 7G:
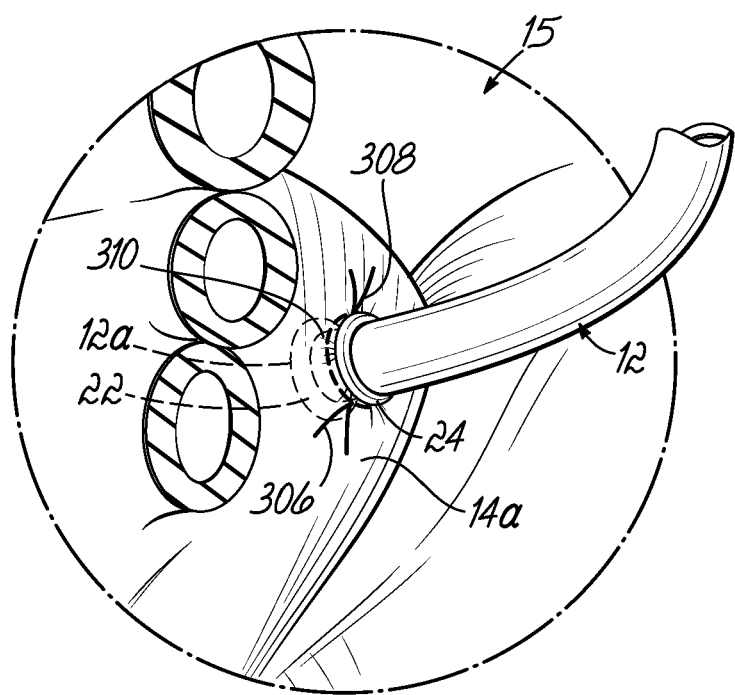
FIG. 7G is an enlarged view of the heart with the insertion device and guidewire removed and with the inflow cannula secured to the left atrial wall of the heart.

At this time, the purse string sutures 306, 308 may be tightened, as illustrated in FIG. 7E and tied off to fully secure the tissue 310 between the distal 22 and proximal 24 anchor elements to provide a fluid tight or at least a substantially fluid tight seal. In this regard, the tightened tissue 310 should at least substantially fill or gather within the gap between the distal and proximal anchor elements 22, 24 as shown in FIG. 7E. If additional gathering of tissue 310 is necessary, additional tissue 310 may be gathered with one or more additional purse string sutures. Anchor elements 22, 24 and the portion of cannula 12 that engages wall 14a may be provided with a tissue ingrowth material to further aide in providing a leak tight seal.

After the sutures 306, 308 are tightened, guidewire 50 and insertion device 200 may be withdrawn as shown in FIG. 7F, leaving the distal end portion 12a of cannula 12 inserted in left atrium 14 and with cannula 12 secured to wall 14a of heart 15 as shown in FIGS. 7F and 7G.

Co-pending U.S. patent application Ser. No. 11/846,886, entitled "Cannula Insertion Devices, Systems, and Methods Including a Compressible Member," now U.S. Pat. No. 8,333,686, which is expressly incorporated by referenced herein in its entirety as noted previously, describes a sealing function of the compressible member 116 of insertion device that advantageously protects against blood loss and/or air ingress into the blood. This same function may be achieved with the inflatable member 224 of insertion device 200 disclosed herein. More specifically, when the inflatable member 224 is sufficiently inflated, it provides a seal with the inner surface of inflow cannula 12. Accordingly, the inflatable member 224 prevents blood loss through inflow cannula 12 when the distal end portion 12a of cannula 12 is inserted into the left atrium 14 and the purse string sutures 306, 308 are tightened to secure cannula 112 to the left atrial wall 14a as described above with reference to FIGS. 7D and 7E.

Additionally, during the process of withdrawing the insertion device 200 from inflow cannula 12, the inflatable member 224 may be partially deflated so that it remains in contact with the inner surface of cannula 12 but allows insertion device 200 to slide relative to cannula 12 (unlike FIG. 7F in which the inflatable member 224 is deflated so that it does not engage the inner surface of cannula 12). In this event, the insertion device 200 acts like a piston that removes air. In particular, the insertion device 200 may create a vacuum as it is retracted to draw blood from heart 15 into the inflow cannula 12. The blood replaces air that previously occupied the inflow cannula 12.

Below, and as representative and nonlimiting examples, various surgical approaches are more fully described and may be used to practice the various aspects described hereinabove.

Surgical Open Sternotomy—

This approach allows full access to the heart, especially the left atrium, and allows access to several different locations where a blood inflow cannula might be attached to the heart. However, due to the highly invasive nature of this approach, less invasive implantation approaches may be more desirable to a surgeon.

Surgical Open Thoracotomy—

In this surgical approach, a relatively superior and caudal thoracotomy access is used to deliver the blood inflow cannula to the left atrium where it is anchored. This location on the atrium has specific benefit because the wall of the atrium is smooth and relatively large at this location, isolating the cannula tip from other structures within the atrium.

In another suitable surgical method, a relatively lateral thoracotomy access is used to deliver the blood inflow cannula to the left atrium where it is anchored at a location on the postero-medial wall near the interatrial septum. This location is often called "Waterson's groove" as discussed above and is a common location to make a left atriotomy when performing mitral valve repair surgery. Waterson's groove terminates between the superior vena cava and the left pulmonary veins at the left atrium.

Thoracoscopic Surgery—

In this surgical method, the blood inflow cannula may be implanted in a similar location as described above in that a tubular trocar may be used to access the intra-thoracic location (Waterson's groove, for example) where the cannula would be anchored through the heart wall. In this minimally or less invasive surgical method, the entire operation is performed through these relatively small tubular trocars thereby minimizing the size of the opening in the patient's chest. Typically, additional small holes are made to deliver trocars used in conjunction with the main delivery trocar to allow placement of an endoscopic camera and specialized surgical tools for grasping, cutting, suturing, cauterizing, or performing other operations on tissue. Through the main trocar, the cannula can be delivered to the same location as in the open surgical technique (i.e. Waterson's groove) but with less invasive access across the chest wall.

Over-the-Wire (Seldinger) Technique

A variation of the Seldinger technique might be utilized in the various surgical implantation approaches described above, where the cannula system would be specifically adapted to facilitate this implantation technique. Although the Seldinger technique is most commonly associated with percutaneous access to blood vessels, an adapted version of the technique utilizing a specifically adapted cannula introduction system is a highly preferred approach to surgical implantation where direct access to the heart itself is utilized. Here, for example, inserting a needle across the heart wall could make an atriotomy and a guidewire could then be placed therethrough. After removal of the needle, with bleeding controlled and minimal, the cannula system with specialized introduction obturator within can be introduced over the wire thereby maintaining many of the advantages of the so-called Seldinger technique even in a surgical approach.

While the present invention has been illustrated by a description of various illustrative embodiments and while these embodiments have been described in some detail, it is not the intention of the Applicants to restrict or in any way limit the scope of the appended claims to such detail. The features and aspects discussed herein may be used in any suitable combination. Additional advantages and modifications will readily appear to those skilled in the art. For example, although the insertion devices disclosed in the embodiments illustrated herein include an inflatable member to releasably secure the respective insertion device to a cannula, alternate insertion devices having other configurations including other expandable members, which are not inflatable members, may be used according to the inventive aspects to temporarily and/or releasably secure the insertion devices to a respective cannula. Examples of such insertion devices are disclosed in previously referenced, co-pending U.S. patent application Ser. No. 11/846,886, wherein the included expandable member is compressible member 116. Compressible member 116 expands radially outward when compressed in an axial direction to releasably secure the respective insertion device to a cannula. Any other suitable expanding member may be used to secure the associated insertion device to a cannula. Also, tip 220 may be used with other insertion devices. For example, tip 220 may be used with insertion devices that do not include inflatable member 224 and/or hub 222. The various features of the invention may be used alone or in any combinations depending on the needs and preferences of the user. However, the invention itself should only be defined by the appended claims.

What is claimed is:

1. A method of inserting an inflow cannula having a lumen into a chamber in a heart of a patient comprising:
    inserting an insertion device into the lumen of the inflow cannula wherein at least a portion of a tip of the insertion device protrudes beyond a distal end portion of the inflow cannula, the insertion device further including a shaft, with the tip being secured to a distal end portion of the shaft, and an expandable member coupled to the distal end portion of the shaft;
    expanding the expandable member to releasably secure the inflow cannula to the insertion device; and
    inserting the tip of the insertion device and the distal end portion of the inflow cannula into the chamber of the heart by pushing the insertion device through a wall of the heart and into the chamber while the inflow cannula is releasably secured to the insertion device.

2. The method of claim 1, further comprising:
    securing the inflow cannula to tissue of the heart defining the chamber; and
    disengaging the expandable member from the cannula after securing the cannula to the heart tissue.

3. The method of claim 2, wherein the expandable member is an inflatable member and wherein:
    expanding further comprises inflating the inflatable member; and
    disengaging further comprises deflating the inflatable member.

4. The method of claim 3, further comprising:
    removing the insertion device from the chamber of the heart and the lumen of the inflow cannula after deflating the inflatable member.

5. The method of claim 3, wherein inflating the inflatable member further comprises:
    directing a pressurized fluid through a lumen formed in the shaft of the insertion device into a hollow interior of the inflatable member.

6. The method of claim 1, further comprising:
    creating a puncture in the tissue defining the chamber; and
    gradually dilating the puncture with the tip of the insertion device to a larger size to facilitate inserting the distal end portion of the inflow cannula into the chamber of the heart.

7. The method of claim 1, wherein the inflow cannula is secured by the expandable member while inserting the tip into the chamber of the heart.

8. A method of inserting an inflow cannula into a chamber in a heart of a patient comprising:
    temporarily securing a distal end portion of an insertion device to a distal end portion of the inflow cannula;
    inserting a tip of the insertion device and the distal end portion of the inflow cannula into the chamber of the heart by pushing the insertion device through a wall of the heart and into the chamber while the inflow cannula is releasably secured to the insertion device;
    inserting the distal end portion of the inflow cannula into the chamber of the heart;
    releasing the distal end portion of the insertion device from the distal end portion of the inflow cannula; and
    withdrawing the insertion device from the inflow cannula.

9. The method of claim 8, further comprising:
    creating an opening in the tissue defining the chamber; and
    gradually dilating the opening with the tip of the insertion device to a larger size to facilitate inserting the distal end portion of the inflow cannula into the chamber of the heart.

10. A method of inserting a cannula having a lumen through biologic tissue comprising:
    inserting an insertion device into the lumen of the cannula wherein at least a portion of a tip of the insertion device protrudes beyond a distal end portion of the cannula, the insertion device further including a shaft, with the tip being secured to a distal end portion of the shaft, and an expandable member coupled to the distal end portion of the shaft;
    expanding the expandable member to releasably secure the cannula to the insertion device; and
    inserting at least the tip of the insertion device and the distal end portion of the cannula through the biologic tissue by pushing the insertion device through the biologic tissue while the inflow cannula is releasably secured to the insertion device.

11. The method of claim 10, wherein the expandable member is an inflatable member and wherein expanding further comprises:
    inflating the inflatable member to releasably secure the cannula to the insertion device.

12. The method of claim 10, wherein expanding further comprises:
    creating an opening in the tissue defining the chamber; and
    gradually dilating the opening with the tip of the insertion device to a larger size to facilitate inserting the distal end portion of the cannula through the tissue.

13. The method of claim 10, wherein the cannula is secured by the expandable member while inserting the tip through the tissue.

* * * * *